United States Patent [19]

Pick

[11] Patent Number: 4,544,774

[45] Date of Patent: Oct. 1, 1985

[54] PROCESS FOR REDUCING COLOR IN POLY(TETRAMETHYLENE ETHER) GLYCOL

[75] Inventor: Rudolph Pick, Dordrecht, Netherlands

[73] Assignee: E. I. Du Pont de Nemours and Company, Wilmington, Del.

[21] Appl. No.: 678,681

[22] Filed: Dec. 5, 1984

[51] Int. Cl.[4] ............................................. C07C 41/34
[52] U.S. Cl. ..................................... 568/617; 568/621
[58] Field of Search ................................ 568/617, 621

[56] References Cited

U.S. PATENT DOCUMENTS

| | | | |
|---|---|---|---|
| 2,751,419 | 6/1956 | Hill et al. | 568/617 |
| 3,358,042 | 12/1967 | Dunlop et al. | 568/617 |
| 3,454,652 | 7/1969 | Dunlop et al. | 568/617 |

*Primary Examiner*—Howard T. Mars

[57] ABSTRACT

The color level of poly(tetramethylene ether) glycol made by catalytically polymerizing tetrahydrofuran using fluosulfonic acid as the catalyst is significantly lower if the fluosulfonic acid contains aluminum.

2 Claims, No Drawings

PROCESS FOR REDUCING COLOR IN POLY(TETRAMETHYLENE ETHER) GLYCOL

DESCRIPTION

1. Technical Field

This invention relates to a method for preparing poly(tetramethylene ether)glycol (PTMEG) having a low level of color.

2. Background and Summary of the Invention

PTMEG is a commodity in the chemical industry, widely used as a raw material in the preparation of polyurethanes.

One of the several methods of preparing PTMEG is the catalytic polymerization of tetrahydrofuran (THF), using fluosulfonic acid (FSA) as the catalyst. PTMEG made this way sometimes has an undesirable yellow cast, which must be reduced or eliminated to meet most commercial specifications.

I have discovered that this yellow coloration can be significantly reduced if the FSA used as the polymerization catalyst contains aluminum.

DETAILED DESCRIPTION

The aluminum can be conveniently incorporated into the FSA by adding an aluminum compound to it. Any aluminum compound can be used which is soluble enough in the FSA to provide the requisite concentration of aluminum. Illustrative are aluminum sulfate, aluminum chloride, aluminum oxide and aluminum fluoride. Aluminum sulfate is preferred. Aluminum metal, preferably in finely divided form, can also be used.

Enough of the aluminum compound is added to the FSA to give an aluminum ion concentration of about 2-1000 ppm, preferably 100-200.* The compound can be added to the FSA at any point before the PTMEG polymerization step, but the addition is most beneficial if it is made just before the FSA is introduced into the polymerization reaction mass.
*As measured by atomic absorption.

The addition itself is simply a matter of bringing the aluminum compound and the FSA together and then stirring or otherwise agitating the mixture until enough of the aluminum compound dissolves.

As an alternative to direct addition, one can store or ship the FSA in an aluminum container. The FSA will dissolve enough aluminum from the container during shipment or storage to give the beneficial effects of the invention. I prefer this method.

FSA treated according to my invention can be used directly in the PTMEG polymerization. No extra process steps or subsequent purification of the polymer are required.

Those skilled in the art will be able to practice this invention more easily after referring to the following illustrative examples.

Those artisans will no doubt be able to compose numerous variations on the theme disclosed, such as changing the amounts of ingredients slightly but insignificantly from those shown, adding innocuous substances, or substituting equivalent or nearly equivalent components for those shown. All these variations are considered to be part of my inventive concept.

In the Examples all parts are by weight.

EXAMPLE 1

THF, 350 parts, was charged to a reactor previously purged with nitrogen. Twenty parts of FSA, that had been shipped and stored in a steel container, were then slowly added below the surface of the THF, with stirring, while the temperature of the reaction mass was held at 35° C.

The mass was then held at 35° C. for four hours, with stirring, after which 200 parts of hot distilled water were added with stirring.

The reaction mass was stripped of unreacted THF by distillation at 100° C., and then washed twice with hot distilled water.

Lime, 2 parts in excess of the amount needed to neutralize, was added to the reaction mass, with vigorous stirring, and the reaction mass was then dried under vacuum at 110°-120° C. and filtered.

The resulting PTMEG had an APHA color of 100.*
*Determined with the American Public Health Association's platinum-cobalt scale, using a Klett-Summerson Industrial Photoelectric Colormeter, No. 42 blue filter, 40 mm path length.

EXAMPLE 2

The procedure of Example 1 was repeated, except that the FSA used had been shipped and stored in an aluminum container, and consequently contained 50 ppm of aluminum.

The resulting PTMEG had an APHA color of 27.

EXAMPLE 3

The procedure of Example 1 was again repeated, except that the FSA contained 200 ppm of aluminum as a result of the addition of aluminum sulfate just before polymerization. The resulting PTMEG had an APHA color of 38.

I claim:

1. In the process of preparing poly(tetramethylene ether)glycol by the catalytic polymerization of tetrahydrofuran using fluosulfonic acid as the catalyst, a method of reducing color formation which comprises using fluosulfonic acid which contains 2-1000 ppm of aluminum.

2. The method of claim 1 wherein the fluosulfonic acid contains 100-200 ppm of aluminum.